United States Patent [19]

Fuller

[11] Patent Number: 5,424,190

[45] Date of Patent: Jun. 13, 1995

[54] METHOD FOR USING AMIDE-CONTAINING STOP SOLUTION

[75] Inventor: Carl W. Fuller, Cleveland Heights, Ohio

[73] Assignee: United States Biochemical Corporation, Cleveland, Ohio

[21] Appl. No.: 121,936

[22] Filed: Sep. 15, 1993

Related U.S. Application Data

[63] Continuation-in-part of Ser. No. 960,169, Oct. 13, 1992, abandoned.

[51] Int. Cl.[6] .......................... C12Q 1/68; C12Q 1/00; C12N 9/99
[52] U.S. Cl. ............................................ 435/6; 435/4; 435/184
[58] Field of Search ..................... 435/6, 4, 184; 564/1

[56] References Cited

U.S. PATENT DOCUMENTS

| | | | |
|---|---|---|---|
| 3,951,755 | 4/1976 | Sartorius et al. | 203/16 |
| 4,079,028 | 3/1978 | Emmons et al. | 260/29.6 NR |
| 4,795,699 | 1/1989 | Tabor et al. | 435/5 |

OTHER PUBLICATIONS

Slonitskii et al., "Influence of Solvent Structure on Interaction of Amides with Native DNA Molecule. II. Aqueous Mixtures of Acetamide", 14 *Molecular Biology* (Moscow), 599–603 1980.

Sambrook et al., *Molecular Cloning: A Laboratory Manual*, 1989 by Cold Springs Harbor-Laboratory Press, pp. 13.3, 13.54, 13.59 and B.25.

Taniewska–Osinska et al., "Viscocimetric Studies of Water–Acetamide System within the temperature range 25–85. degree.C", 1 *Acta Univ. Lodz.* 103, 1982.

*Primary Examiner*—Margaret Parr
*Assistant Examiner*—David Schreiber
*Attorney, Agent, or Firm*—Lyon & Lyon

[57] ABSTRACT

Stop solutions including a compound selected from the group consisting of acetamide, propionamide, butyramide and N-methylacetamide, and methods and kits for their use, e.g., in DNA sequencing.

4 Claims, No Drawings

METHOD FOR USING AMIDE-CONTAINING STOP SOLUTION

BACKGROUND OF THE INVENTION

This application is a continuation-in-part of Fuller, U.S. Ser. No. 07/960,169, filed on Oct. 13, 1992, abandoned, entitled "IMPROVED STOP SOLUTION", hereby incorporated by reference herein.

This invention relates to solutions useful for stopping enzymatic reactions and in particular, stop solutions for DNA sequencing reactions.

It is common in various protocols using enzymatic reagents to stop the activity of the enzymes prior to analysis of their products. For example, when DNA sequencing is performed using the Tabor and Richardson protocol described in U.S. Pat. No. 4,795,699, a stop solution containing 95% (v/v) formamide, 20 mM EDTA, 0.05% (w/v) Bromophenol Blue and 0.05% (w/v) Xylene Cyanol is added to each reaction, prior to placing the reactions onto a DNA sequencing gel formed from 6% (w/v) polyacrylamide and 7M urea. The formamide is provided to denature the DNA and to inactivate the enzymatic activity present in the reaction mixtures so that no further reaction occurs prior to running the sequencing gel. Generally, such stop solutions include a denaturing reagent, such as formamide, an ion-chelating agent, such as EDTA (to remove available magnesium ions which may be required by enzymes for their continued activity), and one or more colored dyes (which aid gel loading and allow the extent of electrophoresis to be readily followed in a DNA sequencing gel). Commonly used dyes include Bromophenol Blue and Xylene Cyanol FF. While all three components of a "stop solution" (denaturant, chelator and dyes) are important, some procedures call for the use of "stop solutions" which lack dyes (for sequencing with fluorescence detection) or which lack chelator (using other steps or methods to inactivate the enzyme or remove metal ions). This application is primarily concerned with the denaturant portion of the solution, the function of which is to denature the nucleic acid prior to loading it onto a denaturing electrophoresis gel. Since the majority of the material in a typical stop solution is the deanaturant (typically 95% v/v), it is convenient to consider this portion of the stop solution as the "solvent" and the chelator, dyes and water (since dyes and chelator are often added as aqueous solutions during preparation) as solutes. Thus, formamide or a mixture of formamide and other compounds will be used as denaturant which may also be mixed with dyes, chelator and water to conveniently combine the three functions.

SUMMARY OF THE INVENTION

This invention relates to provision of a novel stop solution with improved physical characteristics over prior stop solutions. Such stop solutions of this invention are particularly useful in DNA sequencing procedures, especially when the necessary reagents are stored in microtiter plates for the convenience of an end user. Applicant has determined that the major component of prior stop solutions, namely formamide, has a melting point which is disadvantageously around 2° C. Such a low melting point makes it hard to keep the stop solution in a frozen state. If it is not maintained in a frozen state, it may readily contaminate other wells within a microtiter plate, and thus make the plate useless for DNA sequencing procedures. Applicant has discovered that use of reagents having a higher freezing point allows the stop solution to remain frozen even at relatively elevated temperatures, such as around 15° C. and thus allows production of significantly more useful microtiter plate kits for DNA sequencing.

Thus, in a first aspect the invention features a solution which includes a nucleic acid fragment and an uncharged compound having a melting temperature greater than 15° C. which is soluble in both water and formamide, depending on the components used in forming the solution. Formamide may be included to ensure the solution remains liquid at 15° C., rather than solid. Examples of such uncharged compounds include, but are not limited to, acetamide, propionamide, butyramide, and N-methylacetamide. Such solutions may also include one or more dyes (as noted above), and one or more metal chelating agents, such as EDTA, EGTA, or diethylenetriamine-pentaacetic acid. The compound may also be an alcohol, such as ethylene glycol, which is liquid at 15° C. or is liquid in the presence of formamide.

Specifically, it is important that the solution contain a mixture of components which provide a melting temperature between +5° C. and +15° C. or so that the solution is solid at 0° C. and liquid at room temperature (20° C.). One example includes acetamide (40–50% w/v) and water (5% v/v) in formamide.

In a related aspect, the invention features a stop solution which includes a metal chelating agent and an uncharged compound (as described above), with or without a suitable dye. Such stop solutions are useful in stopping enzymatic reactions, such as DNA sequencing reactions.

In another related aspect, the invention features a microtiter plate which includes the solution or stop solution described above, along with one or more reagents suitable for use in DNA sequencing; preferably, the microtiter plate includes all of the components necessary to perform a sequencing reaction, except perhaps the DNA to be sequenced.

In yet another related aspect, the invention features a method for stopping an enzymatic reaction by addition of a solution or stop solution as described above into the enzymatic reaction, preferably in an amount (volume) between about 25–200% (depending on the concentration of the active ingredients) of the volume of enzyme-containing solution. For example, between 25–200 $\mu$l of stop solution is added to 100 $\mu$l of a reaction solution.

In preferred embodiments, the unchanged compound, e.g., acetamide, is provided at a concentration between 25 and 100% w/v) within the solution or stop solution (or as close to 100% as is possible with the other reagents that are provided in the stop solution). Most preferably, the acetamide, or its equivalent, is provided in an amount between 30 and 70% (w/v) dissolved or comixed in formamide and/or water.

In other related aspects, the invention features a kit which includes reagents necessary for DNA sequencing, such as dideoxynucleotides or solutions containing mixtures of deoxynucleotides and/or dideoxynucleotides, and a stop solution as described above in a separate container; and a method for electrophoresis of a nucleic acid, such as DNA or RNA, by firstly mixing a nucleic acid-containing sample with a solution or stop solution as described above, and then loading the mixture created onto a DNA or RNA sequencing gel.

Other features and advantages of the invention will be apparent from the following description of the preferred embodiments thereof, and from the claims.

DESCRIPTION OF THE PREFERRED EMBODIMENTS

The following is an example of an improved stop solution for use in DNA sequencing protocols. This example is not limiting in this invention since such a stop solution can be used with other enzymes sensitive to the active ingredients, such as acetamide. Those skilled in the art will recognize that these other enzymes and stop solutions can be usefully used as described below, and that this example is simply illustrative of the claimed invention. This example states the problem with existing stop solutions, and provides novel stop solutions for use in various enzymatic reactions.

It is known that DNA samples to be loaded onto a denaturing polyacrylamide gel are placed in a solvent and heated to denature the DNA. Typically, 5 μl of a "Stop Solution" is added to a 5 μl DNA sample. (The volumes vary but usually between ½ volume and 5 volumes of Stop Solution are added, most commonly about 1 volume.) Stop Solution will usually contain EDTA (which chelates $Mg^{2+}$, thus inactivating or stopping the activity of most enzymes), one or more tracking dyes (which help the researcher track the progress of electrophoresis), and either formamide or urea to lower the melting temperature of the DNA. A typical stop solution used in the sequencing kits manufactured by United States Biochemical Corporation (USB, Cleveland, Ohio) is 5% (v/v) water, 20 mM EDTA (pH 8.0), 0.05% (w/v) Bromophenol Blue, and 0.05% (w/v) Xylene Cyanol FF, the balance (solvent) is formamide.

For most sequencing reactions it is recommended that 4 μl of this stop solution be added to 6 μl of a reaction mixture. The resulting mixture is heated to 70°-85° C. for 2-30 minutes and loaded onto the sequencing gel.

The freezing or melting point of the major component, formamide, is 2° C. The addition of water (which freezes at 0° C.) and the salts lowers the freezing point to about −10° C. (The actual melting range is about −11° C. to −6° C.).

For a sequencing kit with reagents pre-dispensed in a microtiter plate (e.g., the RAPIDWELL ™ kit of USB), about 5 μl of stop solution is added to a 10 μl termination reaction. The volume of stop solution included in the kit is about 30 μl for each sequencing reaction. This volume of stop solution can easily splash in the well, contaminating the plate cover and possibly neighboring wells if the plate is jarred. Such splashing is avoided during packing, shipping, and handling of the plate by keeping the stop solution frozen. To do this, the plate must be kept below −11° C. when it is handled. While it is possible to keep such plates frozen at all times, it is not convenient, and the time required to cool a large quantity of freshly filled plates to below −11° C. is up to 12 hours.

Stop Solutions

Applicant now provides a new formulation for use as a stop solution that either does not splash readily (by increasing its viscosity), or remains frozen at a more readily maintainable temperature.

The following stop solutions were prepared and tested:

| Stop Solution Solvent (balance is Formamide) | Sequencing Performance | Ease of use for Sample Loading | Score for Drop Test* |
|---|---|---|---|
| None | Excellent | Easy | D |
| 10% (w/v) PEG-6000 | Fair | Easy | D |
| 20% (w/v) PEG-6000 | Fair | Difficult | C |
| 30% (w/v) PEG-6000 | Fair | Difficult | B |
| 50% (w/v) PEG-6000 | Fair | Difficult | A |
| 10% (w/v) PEG-4000 | Fair | Easy | D |
| 20% (w/v) PEG-4000 | Good | Difficult | C |
| 20% (v/v) PEG-1500 | Excellent | Easy | D |
| 30% (v/v) PEG-1500 | Excellent | Easy | C |
| 50% (v/v) PEG-1500 | Fair | Easy | ND |
| 20% (v/v) PEG-600 | Excellent | Easy | D |
| 30% (v/v) PEG-600 | Good | Easy | C |
| 50% (v/v) PEG-600 | Fair | Easy | C |
| 20% (w/v) Sucrose | Excellent | Easy | D |
| 30% (v/v) Glycerol | Poor | Easy | D |
| 50% (v/v) Glycerol | Poor | Easy | B |
| 30% (w/v) Acetamide | Excellent | Easy | A |
| 50% (w/v) Acetamide | Excellent | Easy | A |

All solutions contained 5% (v/v) water, 20 mM EDTA, 0.05% (w/v) Bromophenol Blue and 0.05% (w/v) Xylene Cyanol FF. The solutions with additives were prepared by dissolving the additive (e.g., acetamide) at the concentration shown in formamide. Then 4 ml of 0.5M EDTA (pH 8.0), 0.5 ml of 1% (w/v) Bromophenol Blue and 0.5 ml of 1% (w/v) Xylene Cyanol FF were added to 95 ml of this solution.

The Sequencing Performance scores were as follows: Excellent, no observable difference between this stop solution and the standard solution noted above; Good, minor shadowing or background seen on some bands; Fair, minor shadowing on most bands; Poor, no sequence. All sequences were performed using the protocol for the SEQUENASE 7-deaza-dGTP DNA sequencing kit and M13mp18 template (United States Biochemical Product No. 70990, except for the substitution of stop solution).

The *Drop score was based on the number of times a microtiter plate (Falcon) filled with 30 μl aliquots of frozen stop solution could be dropped at approximately 5-second intervals, upside-down at room temperature (20° C.) before the solution splashed or spilled. Scores were as follows: A, 10 or more; B, 6-10; C, 3-5; D, 0-2; ND, not determined. (PEG is polyethyleneglycol, the number refers to the average molecular weight.)

As seen in the table above, the addition of various polymers can increase the viscosity enough to prevent spillage, but the resulting sample is very difficult to load onto a sequencing gel and the overall performance of that formulation is poor. The addition of acetamide gave good results for all three of the tests listed in the table. This chemical has a structure that is very similar to that of formamide but it is a solid at room temperature with a melting point of 81° C. Thus, the addition of acetamide raises the melting temperature of a mixture of formamide and/or water in a stop solution.

Example 1

Example 1

Acetamide-containing Stop Solution solutions (prepared as above, after appropriate dilution of acetamide in formamide and containing 5% (v/v) water as well as dyes and EDTA) were tested for their utility in a sequencing protocol, and their approximate melting points determined. (No attempt was made to record the actual melting range, but melting occurs over a range of 5°-7° C.).

| Acetamide Concentration (w/v) | Approx. Melting Temperature |
| --- | --- |
| 0% | −11° C. |
| 30% | −7° C. |
| 50% | 0° C. |
| 60% | 7° C. |
| 70% | >25° C. |

The improvement in the drop-test performance of the stop solutions containing acetamide is probably the result of the increase in melting temperature, because it takes longer to thaw.

In addition to the above DNA sequencing tests, the acetamide-containing stop solutions were also tested for sequencing using plasmid templates and nucleotide mixes containing dGTP and dITP. They were also tested in microtiter-format DNA sequencing kits. There was no difference observable between normal (formamide-only) stop solution and ones containing 50% (w/v) acetamide.

Other materials which can be used in place of acetamide include compounds which are not charged, which have a melting point above 15° C. and are freely soluble in water and formamide, e.g., propionamide, butyramide, and N-methylacetamide (e.g., as solvent without formamide).

These reagents may be used alone or in combination with one another or with formamide or urea.

The invention features use of any such reagents with various kits designed for DNA sequencing (e.g., containing in separate nucleotide wells or containers, dideoxynucleotide-containing solutions, dNTP-containing solutions, nucleic acids, dyes, DNA polymerases, RNA polymerases, and other enzymes, chelating agents and buffers) or other enzymatic procedures. Such dyes can be any standard dye used for such reactions (e.g., at 0.01–0.1% w/v), and such chelating agents can be those used in any standard enzyme-inactivating reaction (e.g., at 1–50 mM).

Other embodiments are within the following claims.

I claim:

1. A method for stopping an enzymatic reaction comprising providing a reagent selected from the group consisting of acetamide, propionamide, butyramide, and N-methylacetamide; wherein said enzymatic reaction used neither, as its substrate or as its product, acetamide, propionamide, butyramide, and N-methylacetamide; and mixing the reagent with the enzymatic reaction solution for a time and in an amount sufficient to stop said reaction.

2. The method of claim 1, wherein the reagent is provided in an amount between 25% (w/v) and 100% (w/v) to said reaction.

3. The method of claim 1, wherein the enzymatic reaction is a DNA sequencing reaction.

4. A method for electrophoresis of a nucleic acid comprising mixing said nucleic acid with a solution comprising a reagent selected from the group consisting of acetamide, propionamide, butyramide, and N-methylacetamide, and loading said mixture onto an electrophoretic gel.

* * * * *

UNITED STATES PATENT AND TRADEMARK OFFICE
CERTIFICATE OF CORRECTION

PATENT NO. : 5,424,190
DATED : June 13, 1995
INVENTOR(S) : Carl W. Fuller

It is certified that error appears in the above-indentified patent and that said Letters Patent is hereby corrected as shown below:

Column 3, line 48, replace "RAPIDWELL TM" with --RAPIDWELL<sup>TM</sup>--.

Column 3, line 61, replace "Stop Solutions" with --Stop Solutions--.

Column 4, line 62, before "solutions" insert --A series of mixtures of acetamide-containing stop--.

Signed and Sealed this

Twenty-third Day of July, 1996

Attest:

BRUCE LEHMAN

Attesting Officer    Commissioner of Patents and Trademarks